United States Patent [19]

Keith

[11] Patent Number: 4,944,765
[45] Date of Patent: Jul. 31, 1990

[54] PROSTHETIC DRIVE DEVICE FOR ROTATABLE TOOL

[76] Inventor: Danny M. Keith, General Delivery, Broadford, Va. 24316

[21] Appl. No.: 325,999
[22] Filed: Mar. 20, 1989
[51] Int. Cl.⁵ .............................................. A61F 2/54
[52] U.S. Cl. ...................................... 623/65; 623/63
[58] Field of Search ................................ 623/65, 57, 63

[56] References Cited

U.S. PATENT DOCUMENTS

| | | | |
|---|---|---|---|
| 1,318,260 | 10/1919 | Bosch | 623/69 |
| 1,323,671 | 12/1919 | Baehr | 623/65 |
| 1,989,960 | 2/1935 | Wheeler | 623/69 |
| 2,416,030 | 2/1947 | Vesper | 623/65 |
| 2,666,928 | 1/1954 | Ameline | 623/69 |
| 3,490,078 | 1/1970 | Perez | 623/65 |
| 3,656,187 | 4/1972 | Katz | 623/65 |
| 3,802,302 | 4/1974 | Bengston | 623/65 |
| 3,965,491 | 6/1976 | Frenzel | 623/65 |
| 4,159,545 | 7/1979 | Manning | 623/65 |
| 4,661,113 | 4/1987 | Adkins | 623/65 |

Primary Examiner—Randall L. Green
Assistant Examiner—David H. Willse

[57] ABSTRACT

An artificial arm device having a prosthetic member adapted to be affixed to an arm segment for movement therewith, a tool drive device affixed to the prosthetic member and having a tool holder rotatably mounted thereon, a lever engaging the tool holder, and a body strap having one end segment adapted to be operator body mounted and having its outer end segment affixed to the lever, whereby relative motion between the operator's body and the arm segment will tension the strap and cause the lever to rotate the tool holder and a tool mounted thereon.

14 Claims, 2 Drawing Sheets

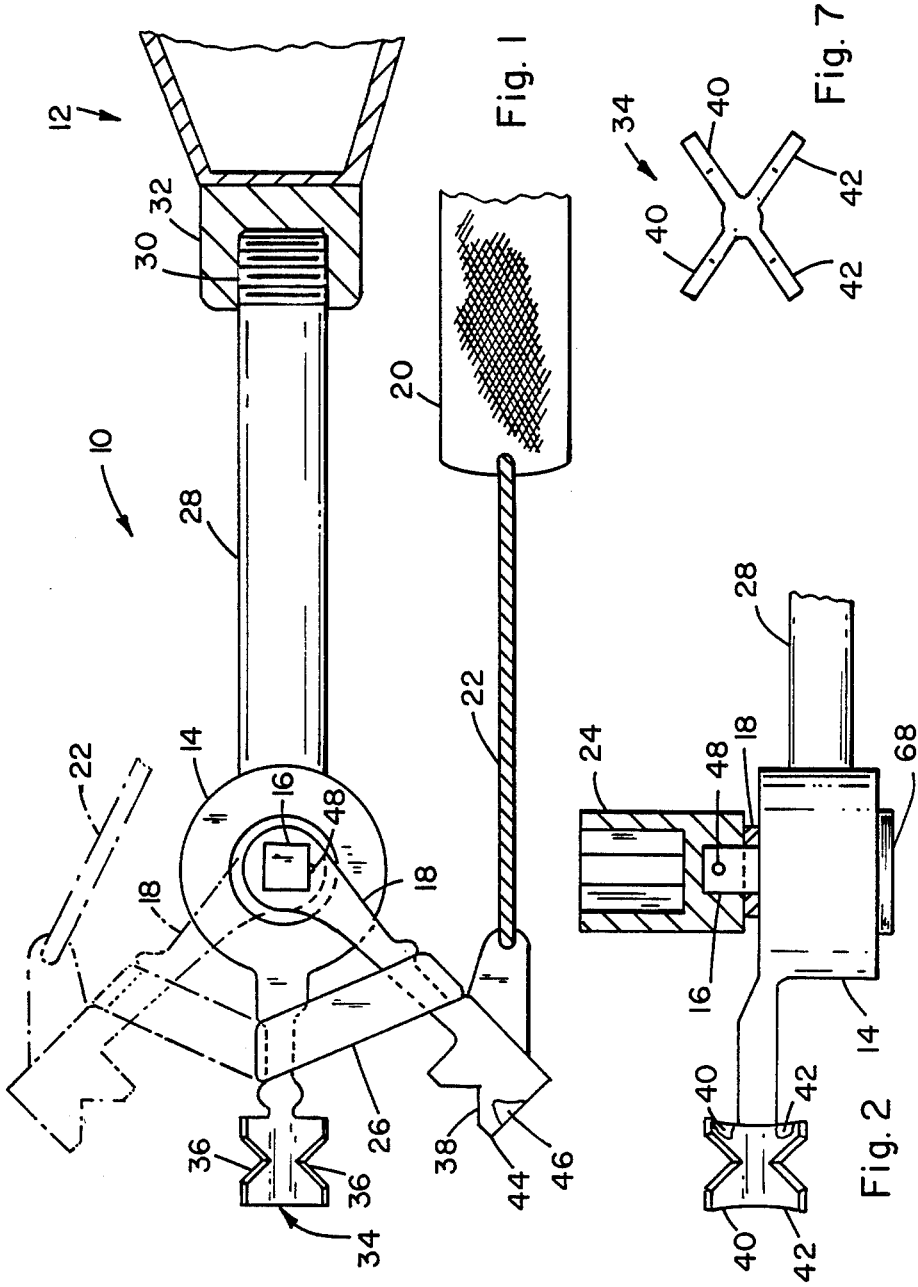

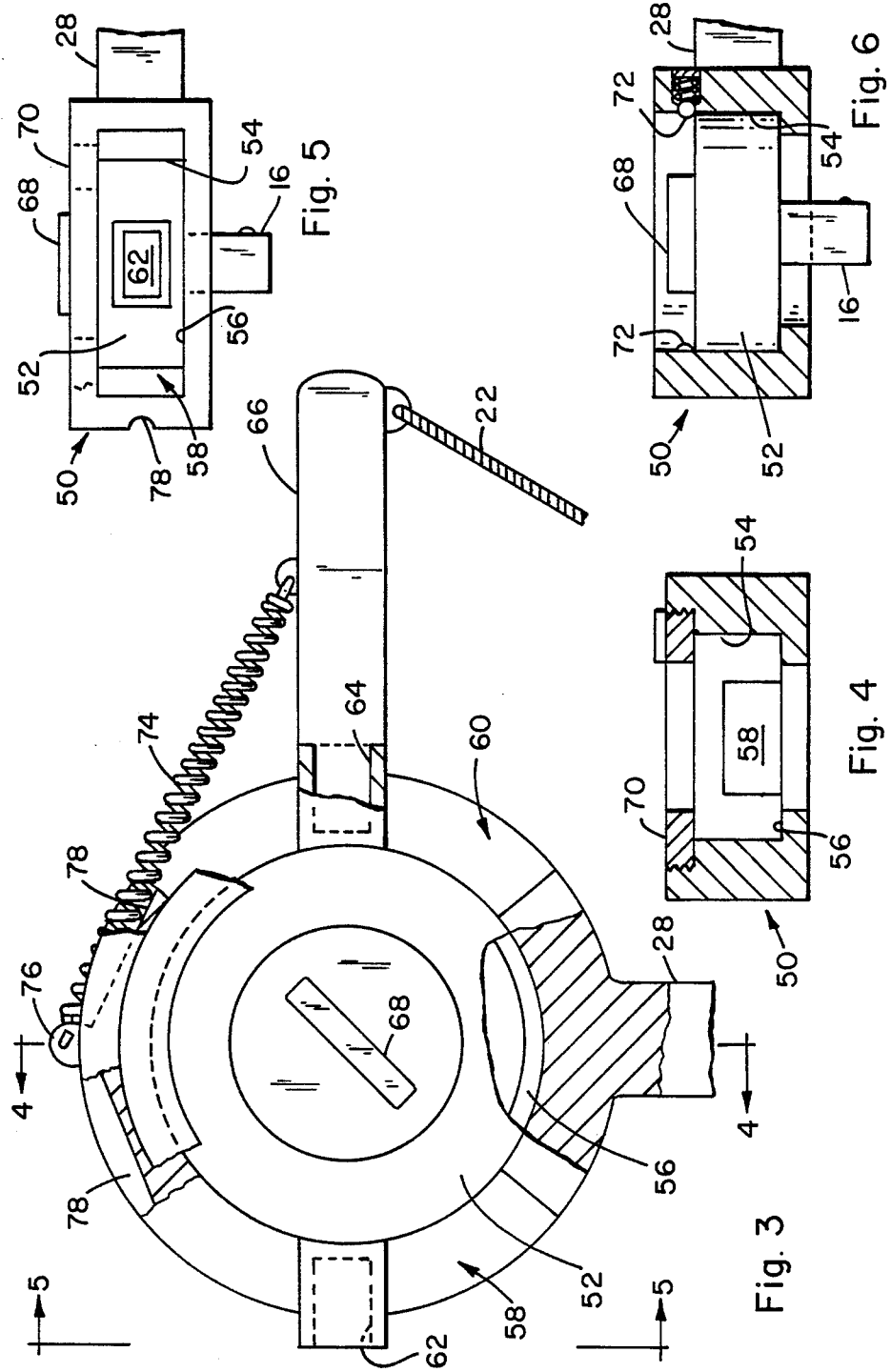

PROSTHETIC DRIVE DEVICE FOR ROTATABLE TOOL

This invention concerns an artificial arm device which is specially constructed to provide for the operation of tools such as wrench sockets, wrench type screw drivers, or the like, and especially concerns such a device which is readily operable by conventional prosthetic shoulder strap means.

Heretofore, the use of artificial arm devices for such tasks as operating wrenches or the like for tightening or removing bolts has been very limited as the forces required often dislocate the artificial arm devices from the operator's arm segment. Such would be the case, for example, with the devices shown in U.S. Pat. Nos. 3,802,302; 493,440; 396,061; 1,050,607; and 3,538,515 the disclosures of which are incorporated herein by reference to show the strap and cable mechanisms typically employed to actuate various gripping elements of prosthetic arm devices.

A principal object therefore of the preent invention is to provide a prosthetic arm device which is so constructed that it can be operated in a normal manner for operating such prosthetic devices, but which can generate the large forces required for wrenching bolts and the like without dislocating the device from the arm segment.

This and other objects and advantages are achieved in accordance with the present invention through the novel structure of a tool drive device adapted for attachment to and use with an artificial arm prosthetic member adapted to be affixed to an arm segment for movement therewith, said tool drive means comprising body means, tool holder means rotatably mounted on said body means, lever means engaging said holder means and adapted to be attached to one end of body strap means the other end of which is operator body mounted, whereby relative motion between said operator body and said arm segment will tension said strap means and cause said lever means to rotate said tool holder means relative to said tool body means.

In certain preferred embodiments:

the lever means is continually urged to an initial position by resilient return means;

the holder means is a wrench socket key stud;

the operator body includes the opposite shoulder;

a gripping member is provided on said device, and said resilient return means is cooperatively provided on said device and said lever means for forcing a segment of said lever means into close proximity to said gripping member upon relaxation of said tensioning;

the tool holder means and said body means are provided with cooperating ratchet means whereby relaxation of said tensioning will allow return of said lever means to said initial position while allowing said holder means to remain in its rotated position; and the body means is provided with a retainer housing adapted to receive the head of a ratchet wrench and provide bearing means for rotation thereof, wherein said tool holder means is the key stud of the ratchet wrench and wherein said lever means is the ratchet wrench handle.

The invention will be further understood from the following drawings and description thereof wherein:

FIG. 1 is an elevational view of the bottom or stud side of the present tool drive device with the lever in an advanced ratchet swing position;

FIG. 2 is a side view of the head portion of the drive device of FIG. 1 with the mounting portion of the lever shown in cross-section;

FIG. 3 is an enlarged partial sectional top view of a variation of the drive device provided with a conventional reversible ratchet mechanism with the lever or handle approximately in its mid ratchet swing position;

FIG. 4 is a reduced dimension cross-sectional side view of the ratchet wrench head retainer housing of FIG. 3 taken along the line 4—4 in the direction of the arrows;

FIG. 5 is a reduced dimension view of the device of FIG. 3 taken along line 5 thereof in the direction of the arrows;

FIG. 6 is a cross-sectional view as in FIG. 4 showing the use of a detent ball retainer for the wrench head; and FIG. 7 is an end view of the gripping flanges of the body of the drive device.

Referring to the drawings and with specific reference to claim 1 hereof, the present tool drive device generally designated 10 is adapted for attachment to and use with an artificial arm prosthetic member 12 adapted to be affixed to an arm segment for movement therewith, said drive device comprising body means 14, tool holder means 16 rotatably mounted on said body means, lever means 18 engaging said holder means, and body strap means 20 having one end segment adapted to be operator body mounted in conventional manner and having its other end segment or cable 22 affixed, preferrably pivotably, to said lever means, whereby relative motion between said operator body and said arm segment will tension said strap means and cause said lever means to rotate said tool holder relative to said tool body means.

In the embodiment shown in FIGS. 1 and 2 the tool drive means 10 is essentially a conventional ratchet socket wrench; the stud 16 of which is freely rotatable when the ratchet mechanism is removed. With such a construction, the key stud 16 is removed from, e.g., a socket 24; each time it is rotated by the lever 18 and is then replaced on the socket after the lever and stud have been rotated back to their initial positions by the action of the resilient return means such as the conventionally employed heavy rubber band 26.

The handle 28 of the wrench is conveniently threaded at 30 to provide an easy attachment to the internally threaded socket end 32 of the prosthetic member 12. A gripping member 34 is preferably provided on body 14 extending generally axially of handle 28 and prosthetic member 12. Member 34 and lever 18 are preferably provided with aligned notches or recesses 36 and 38, and preferably in dual flanges 40, 42 and 44, 46 respectively. This gripping construction has been found especially useful for picking up tools, sockets, and the like. It is seen that when it is desired to reverse the rotational direction of the stud 16, it is merely necessary to forcibly slide the lever 18 up over the detent ball 48, reverse the position of the lever by turning it over and replacing it back over the stud and detent ball in the position shown by the dotted lines in FIG. 1. No detatchment or rearrangement of the resilient return means 26 or of the cable 22 of the body strap means is required for this reversal as their points of attachment are preferably universally pivotably constructed.

Referring to FIGS. 3-6, a preferred embodiment of the present device is shown as comprising a retainer housing generally designated 50 adapted to provide bearing means for rotatably supporting the head 52 of a conventional reversible ratchet wrench such as shown and described for example, in U.S. Pat. Nos. 2,701,977; 2,957,377; 2,978,081; 3,290,969 and 3,372,612, the disclosures of which are incorporated herein by reference. The housing is formed to the general shape of a shallow cylinder having a cylindrical inner side wall 54 providing a rotational bearing surface, and an annular bottom 56 providing a stop means. The side wall 54 is provided with ports 58 and 60 for accomodating removable wrench handle sockets. The wrench head 52 is rotationally positioned in the housing with sufficient clearance with wall 54, bottom 56 and retainer ring 70 or detent balls 72 to allow free rotation of the head through a typical ratchet cycle. The particular wrench head shown in FIGS. 3, 5 and 6 is a conventional ratchet wrench head modified to provide two handle sockets 62 and 64 into which a handle or lever such as 66, equivalent to lever 18, can be readily inserted and held by suitable means such as a conventional detent ball. The purpose of such dual handle sockets is to provide an extremely simple means for reversing the direction of rotation of the stud 16. This is readily accomplished by pulling the handle 66 from socket 64, reversing its direction, i.e., repositioning it 180° with respect to housing 50, inserting it into socket 62 and reversing the ratchet direction of the wrench head by means of the conventional ratchet turnkey 68 in normal fashion. With this construction it is not necessary to remove the retainer cap 70 or similar retainer to allow removal of the wrench head from the retainer housing 50 in order to 180° reposition it, which would be the case where an ordinary, one handle ratchet wrench is employed. However, a quick access retainer construction could be employed such as the spring urged detent balls 72 mounted in housing 50 as shown in FIG. 6. With such detent construction, in order to remove the conventional ratchet wrench from the housing 50 it is only necessary to apply force to the end of stud 16 to pop the wrench head past the detent balls. In the embodiment of FIGS. 3-6, the resilient return means may conveniently be a coiled extension spring such as 74 pivotally connected to handle 66 or to a conventional ratchet wrench handle, and to a suitable nib 76 on the housing periphery. It is preferable to provide slots such as 78 in the housing periphery to slidably contain the spring for smooth operation.

Housing 50 may of course be modified both in configuration and dimensions in order to accommodate various sizes and shapes of ratchet wrench heads, and the ratchet mechanism may also be an intrinsic part of the housing, particularly where the dual handle socket embodiment of FIG. 3 is contemplated. Housing 50 may, of course, also be provided with a gripping means such as member 34.

The invention has been described in detail with particular reference to preferred embodiments thereof, but it will be understood that variations and modifications will be effected within the spirit and scope of the invention.

I claim:

1. A tool drive device adapted for attachment to and use with an artificial arm prosthetic member adapted to be affixed to an arm segment for movement therewith, said tool drive comprising tool body means, tool holder means rotatably mounted on said tool body means, lever means engaging said holder means and adapted to be attached to one end of body strap means the other end of which is operator body mounted, whereby relative motion between said operator body and said arm segment will tension said strap means and cause said lever means to rotate said tool holder means relative to said tool body means.

2. The device of claim 1 wherein said lever means is continually urged to an initial position by resilient return means.

3. The device of claim 2 wherein said holder means is a socket key stud.

4. The device of claim 3 wherein said operator body includes the opposite shoulder.

5. The device of claim 4 wherein a gripping member is provided on said tool body means, and said resilient return means is cooperatively provided on said tool body means and said lever means for forcing a segment of said lever means into close proximity to said gripping member upon relaxation of said tensioning.

6. The device of claim 5 wherein said resilient return means comprises a spring element stretched between said gripping member and said lever means.

7. The device of claim 6 wherein said spring element is a rubber band.

8. The device of claim 7 wherein said gripping member is a projection on said tool body means extending outwardly from said stud generally axially of said prosthetic member.

9. The device of claim 8 wherein juxtaposed surfaces of said gripping member and said lever means provide recess means in which an article can nest for gripping.

10. The device of claim 2 wherein said tool holder means and said tool body means are provided with cooperating ratchet means whereby relaxation of said tensioning will allow return of said lever means to said initial position while allowing said holder means to remain in its rotated position.

11. The device of claim 1 wherein said tool body means is provided with a retainer housing adapted to receive the head of a reversible ratchet wrench and provide bearing means for rotation thereof, wherein said tool holder means is the key stud of the ratched wrench and wherein said lever means is the handle of the ratchet wrench.

12. The device of claim 2 wherein said tool body means is provided with a retainer housing adapted to receive the head of a reversible ratchet wrench and provide bearing means for rotation thereof, wherein said tool holder means is the stud of the ratchet wrench and wherein said lever means is the handle of the ratchet wrench.

13. The device of claim 3 wherein said sochet key stud is provided with ball detent means and said lever means is provided with an aperture of mating configuration with said key stud configuration such that said lever means can be forced over said detent means to allow reversal of said lever means and reversal in the direction of rotation of said key stud.

14. The device of claim 11 wherein said wrench head is provided with substantially oppositely circumferentially disposed handle means, and said retainer housing is provided with substantially oppositely circumferentially disposed handle ports for accommodating ratchet swing motion of said handle means.

* * * * *